United States Patent
Smith et al.

(10) Patent No.: US 8,920,517 B2
(45) Date of Patent: Dec. 30, 2014

(54) MODELING AND DESIRED CONTROL OF AN ENERGY-STORING PROSTHETIC KNEE

(75) Inventors: William A. Smith, Lyndhurst, OH (US); Sergey Samorezov, Highland Hts., OH (US); Brian L. Davis, Moreland Hills, OH (US); Antonie J. van den Bogert, Cleaveland Hts., OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 190 days.

(21) Appl. No.: 13/464,170

(22) Filed: May 4, 2012

(65) Prior Publication Data

US 2013/0013085 A1   Jan. 10, 2013

Related U.S. Application Data

(60) Provisional application No. 61/482,445, filed on May 4, 2011.

(51) Int. Cl.
| | | |
|---|---|---|
| *A61F 2/48* | (2006.01) | |
| *A61F 2/68* | (2006.01) | |
| *A61F 2/64* | (2006.01) | |
| *A61F 2/74* | (2006.01) | |
| *A61F 2/50* | (2006.01) | |
| *A61F 2/70* | (2006.01) | |

(52) U.S. Cl.
  CPC ............ *A61F 2/64* (2013.01); *A61F 2002/744* (2013.01); *A61F 2002/748* (2013.01); *A61F 2/68* (2013.01); *A61F 2002/74* (2013.01); *A61F 2002/5006* (2013.01); *A61F 2002/701* (2013.01); *A61F 2002/704* (2013.01)
  USPC .............................................. 623/24; 623/45

(58) Field of Classification Search
  USPC ............................................. 623/24, 39–46
  See application file for complete search history.

(56) References Cited

U.S. PATENT DOCUMENTS

| 5,092,902 A | 3/1992 | Adams et al. |
|---|---|---|
| 6,740,125 B2 | 5/2004 | Mosler |
| 7,279,009 B2 | 10/2007 | Herr et al. |
| 7,549,969 B2 | 6/2009 | van den Bogert |

(Continued)

FOREIGN PATENT DOCUMENTS

DE    10 2008 045113 A1    3/2010

OTHER PUBLICATIONS

PCT International Search Report and Written Opinion, dated Jul. 30, 2012, pp. 1-12.

(Continued)

*Primary Examiner* — Bruce E Snow
(74) *Attorney, Agent, or Firm* — Tarolli, Sundheim, Covell & Tummino LLP

(57) ABSTRACT

An energy-storing prosthetic knee includes an upper leg structure and a lower leg structure hingedly connected to the upper leg structure. The lower and upper leg structures move pivotally relative to one another. A fluid actuator is operatively connected to the upper and lower leg structures such that relative pivotal movement of the upper and lower leg structures causes a fluid to flow in a predetermined manner within the fluid actuator. At least two controllable variable fluid flow resisting devices, an accumulator, and a control system are also provided. The control system is actuable to cause storage of the fluid energy for a predetermined length of time and release of the fluid energy at a predetermined time during the gait cycle. Both the storage and release of the fluid energy are variable by action of the control system without physical modification of other components of the prosthetic knee.

10 Claims, 13 Drawing Sheets

(56) References Cited

U.S. PATENT DOCUMENTS

| | | | |
|---|---|---|---|
| 7,731,759 | B2 | 6/2010 | Pusch et al. |
| 7,785,373 | B2 | 8/2010 | Frye, Jr. |
| RE42,903 | E | 11/2011 | Deffenbaugh et al. |
| 2006/0235544 | A1 | 10/2006 | Iversen et al. |
| 2006/0249315 | A1 | 11/2006 | Hugh et al. |
| 2006/0293761 | A1 | 12/2006 | Baumann et al. |
| 2009/0037000 | A1 | 2/2009 | Frye, Jr. |
| 2010/0023133 | A1 | 1/2010 | Fairbanks et al. |
| 2011/0098828 | A1 | 4/2011 | Balboni et al. |

OTHER PUBLICATIONS

Richter H, 2010a. "Motion Control of a Container with Slosh: Constrained Sliding Mode Approach," ASME Journal of Dynamic Systems, Measurements and Control, vol. 132.

Anderson F and Pandy M, 2001. "Dynamic optimization of human walking," Journal of Biomechanical Engineering, vol. 123, pp. 381-390.

Martinez-Villalpando E et al., 2009. "Agonist-antagonist . . . level-ground walking," Jnl of Rehab Research and Devel, vol. 46, pp. 361-373.

van den Bogert A, Samorezov S, Davis B, and Smith W, 2011a. "Modeling and optimal control of an energy-storing prosthetic knee," 23rd Congress of the International, pp. 1-10.

Slotine J. and Li W, 1987. "On the adaptive control of robot manipulators," International Journal of Robotics Research, vol. 63, pp. 147-157.

Seroussi R, et al., 1996. "Mechanical work adaptations of above-knee amputee ambulation," Archives of Physical Medicine and Rehabilitation, vol. 77, pp. 1209-1214.

Segal A, et al., 2006. Kinematic and kinetic . . . Mauch SNS Prosthetic Knees, Jnl of Rehab. and Dev, vol. 43, pp. 857-870.

Richter H and Maynard R, 2010b. "Hybrid-Dynamical Modelling . . . Clutch," Proceedings of the Institution , vol. 244, pp. 361-372.

Richter H, 2009. "Feasibility of Piezoelectric Actuation . . . Approach," Journal of Intelligent Materials, Systems and . . . , vol. 20, pp. 1259-1266.

Nadeau S, et al., 2003. "Frontal and sagittal . . . level walking?" Clinical Biomechanics, vol. 18, pp. 950-959.

Ma H, et al., 2011. "Blended biogeography . . . optimization," Engineering Applns of Artificial Intelligence, vol. 24, pp. 517-525, http://embeddedlab.csuohio.edu/BBO.

Johansson J, et al., 2005. "A clinical . . . knee devices," American Journal of Physical Medicine and Rehabilitation, vol. 84, pp. 563-575.

Halloran J, et al., 2010. "Concurrent musculoskeletal . . . loading," Journal of Biomechanics, vol. 43, pp. 2810-2815.

Gailey R, et al., 2008. "Review of secondary . . . prosthesis use," Journal of Rehabilitation Research and Development, vol. 45, pp. 15-29.

Chin T, et al., 2006. "Comparison of different . . . amputees: Intelligent knee prosthesis (IP) versus C-leg," Prosthetics and Orthotics International, vol. 30, pp. 73-80.

Bellmann M, et al., 2010. "Comparative biomechanical analysis . . . knee joints," Archives of Physical Medicine and Rehabilitation, vol. 91, pp. 644-652.

van den Bogert A, et al., 2011b. "Implicit methods . . . optimal control," Procedia International Union of Theoretical and Applied Mechanics, vol. 2, pp. 257-316.

van den Bogert A, et al., 2012. "Predictive musculoskeletal . . . and running," Proc. of the Inst. of Mech. Engineers, Part P: Journal of Sports Eng. and Techn., pp. 124-133.

Wilmot T, 2011. Intelligent Controls . . . Knee, CSU, master's thesis, http://www.csuohio.edu/engineering/ece/research/thesis.html., pp. 1-100.

Sup F, et al., 2008. "Design and Control of an Active Elect. Knee and Ankle Prosthesis," IEEE Intl Conf. on Biomedical Rob. and Biomechatronics, Scottsdale, AR, pp. 523-528.

Richter H, et al., 2007. "Robust Positively Invariant Cylinders for Constrained Variable Structure Control Designs," IEEE Transactions on Aut. Control, vol. 53, pp. 2058-2069.

Laferrier, et al. "Advances in Lower-Limb Prosthetic Technology", Phys Med Rehabil Clin N. Am 21 (2010) 86-110.

Kraij, et al. Analysis of Stand. Up and Sitting Down . . . Presentation, J. Biomechanics vol. 23. No. 11, pp. 1123-1138, 1990.

Dosen, et al., Acceleromtrs and Force Sensing Resistors . . . Hemiplegic, IEEE Transactions on BioMechn. Engin., vol. 55. No. 8, Aug. 2008.

Wilmot, et al., "Biogeography-Based Optimi. For Hydraulic Prost. Knee Ctrl", from http://embeddedlab.csuohio.edu/BBO/BBO_Papers/Wilmot2011.pdf. Last accessed Sep. 7, 2012, pp. 1-26.

Bogert, "Exotendons for Assist, of Human Locomotion", from http://www.biomedical-engineering-online.com/content/2/1/17, last accessed Sep. 7, 2012, pp. 1-5.

Johansson,MS, et al., A Clinical Comparison of Variable-Damping and Mechanically Passive Prosthetic Knee Devices, Rapid Comm., Aug. 2005, pp. 663-575.

Gailey, Ph.D., et al., Review of Secondary Physical Conditions Associated with Lower-Limb Amputation and Long-Term Prosthesis Use, JRRD, 2008, pp. 15-30, vol. 45, No. 1.

Chin, et al., Comparison of Different Microprocessor Controlled Knee Joints on the Energy . . . , Prosthetics and Orthotics Int'l., Apr. 2006; 30(1): 73-80, Taylor & Francis.

Ackermann, et al., Optimality Principles for Model-Based Prediction of Human Gait, 2010, Journal of Biomechanics 43, 1055-1060.

Bogert, et al., Optimal Feedback Control for Human Gait with . . . , Sym 101-02: Terrestrial Locomotion, 1-2, http://cms.inmeet.com/Imabstract/SubDetail.aspx.

Laferrier, et al., Advances in Lower-limb Prosthetic Technology, Phys Med Rehabil Clin N m 21 (2010) 86-110, Elsevier Inc.

Kralj, et al., Analysis of Standing Up and Sitting Down in Humans: . . . , J. Biomechanics, vol. 23, No. 11 pp. 1123-1138, 1990, Pergamon Press plc.

Martinez-Villalpando, et al., Agonist-Antoagonist Active Knee Prosthesis: A Preliminary . . . , vol. 46, No. 3, 2009, pp. 361-374.

Seroussi, et al., Mechanical Work Adaptations of Above-Knee . . . , Arch Phys, Med Rehabil., vol. 77, Nov. 1996, pp. 1209-1214.

Lay, et al., The Effects of Sloped Surfaces on Locomotion . . . , J.Jbiomech., 2006, pp. 1621-1628, Elsevier.

Segal, MS, et al., Kinematic and Kinetic Comparisons of Transfemoral . . . , JRRD, vol. 43, No. 7, pp. 857-870, Dept. of Veterans Affairs.

S. Nadeau, et al., Frontal and Sagittal Plane Analyses of the Stair Climbing . . . , Clinical Biomechanics, 18 (2003), pp. 950-959, Elsevier.

Modan, et al., Increased Cardiovascular Disease Mortality . . . , 1998, pp. 1242-1247, Excerpta Modica, Inc.

Sup, et al., Design and Control of an Active Electrical . . . , Conf. Biomed Robot Biomechatron, 2008, 10-19; 2008: 523-528, doi: 10.1109/BIOROB.2008.4762811, pp. 1-20, IEEE.

Bellmann, et al., Comparative Biomechanical Analysis of . . . , Arch Phys Med Rehabil, vol. 91, Apr. 2010.

Winter, et al., Energy Generation and Absorption at the Ankle . . . , Dept. of Kinesiology, Univ. of Waterloo, pp. 147-154, J.B. Lippincott Co.

PCT International Search Report and Written Opinion, mailed Jul. 30, 2012, pp. 1-12.

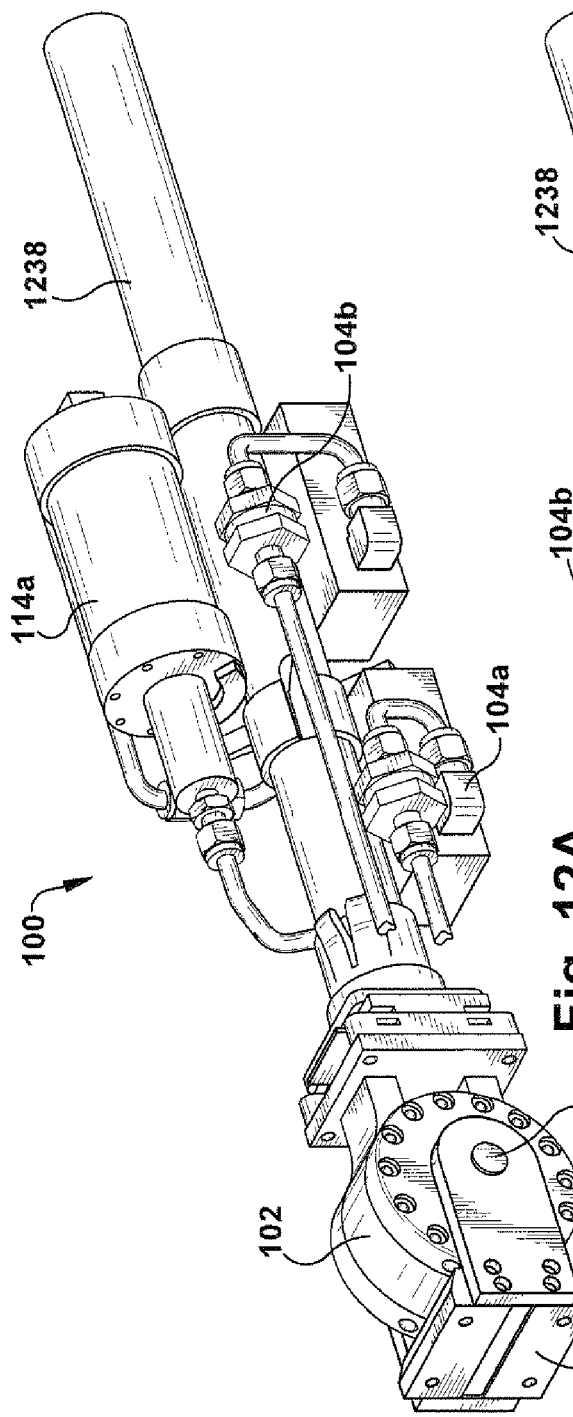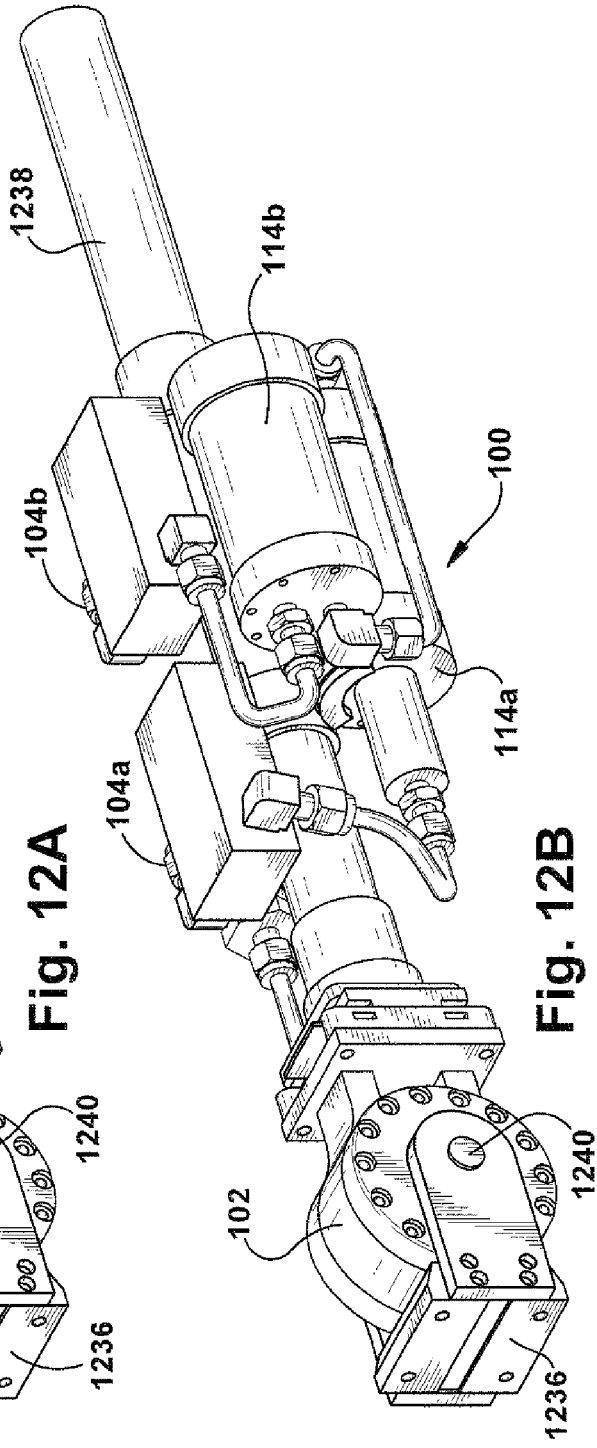
Fig. 12A
Fig. 12B

MODELING AND DESIRED CONTROL OF AN ENERGY-STORING PROSTHETIC KNEE

RELATED APPLICATION

This application claims priority from U.S. Provisional Application No. 61/482,445, filed 4 May 2011, the subject matter of which is incorporated herein by reference in its entirety.

TECHNICAL FIELD

The present invention relates to an apparatus and method for use of a prosthetic knee and, more particularly, to modeling and desired control of an energy-storing prosthetic knee.

BACKGROUND OF THE INVENTION

The energy cost of walking is 30-50% higher in unilateral transfemoral amputees than in able-bodied controls, and at least half of this is due to the loss of knee function. Modern commercial knees with microprocessor-controlled damping mechanisms, such as the Rheo Knee (available from Össur Americas of Foothill Ranch, Calif.) and C-Leg (available from Otto Bock US of Minneapolis, Minn.), have only reduced the energy cost by 3-5%, compared to conventional passive prosthetic mechanisms. This suggests that an essential aspect of knee function is still missing. In studies of transfemoral amputee gait mechanics, it is noticeable that all prosthetic technologies (including microprocessor-controlled dampers) cause the patient to walk without knee flexion during the stance phase, whereas able-bodied subjects have about 15 degrees of flexion-extension movement. Stance phase knee flexion is one of the "six determinants of gait", and although its importance is still debated, its consistent presence in able-bodied gait suggests that it is useful. Indeed, when able-bodied subjects are prevented from flexing their knee during the stance phase, they use 25% more energy for walking. Lack of stance phase knee flexion may also be responsible for gait asymmetry and compensatory strategies such as increased hip muscle forces, possibly leading to overuse injuries and osteoarthritis.

Even though controlled damper devices are designed to allow stance phase knee flexion, patients seem to avoid using this feature. This may be partly due to a lack of confidence in the stability of the limb against buckling. Another explanation may be the considerable relative movement between socket and residual limb, which makes the limb perhaps too compliant, even with a stiff knee. A third possible explanation is that a damper device will dissipate a considerable amount of energy when allowing a controlled flexion during the stance phase, and is not able to produce the required positive work for the subsequent knee extension. The hip extensors would be entirely responsible for bringing the knee back to extension during mid to late stance and for restoring the lost energy. While this strategy for achieving a kinematically normal gait is theoretically possible, it would be kinetically abnormal and require extraordinary effort, so it is understandable that patients seem to avoid this.

The lack of positive work for knee extension often poses a greater challenge for amputees participating in other activities besides level walking. During able-bodied running, there is about 40 degrees of stance phase flexion-extension, which is probably not feasible for users of current prosthetic devices based on what has been observed during walking. This requires transfemoral amputees to run with extreme asymmetries and they accordingly cannot approach able-bodied running speeds. Sit-to-stand is an important function, and transfemoral amputees perform this movement with near-normal kinematics but without any joint moment in the prosthetic knee, i.e., entirely powered by the sound leg. This is inevitable because controlled dampers cannot produce a knee extensor moment while the knee is extending. The most severe functional deficits are found during activities that require net positive work, such as walking uphill and stair ascent. Stair ascent requires large amounts of positive work at the knee which cannot be delivered with controlled damper devices. Consequently, transfemoral amputees are typically seen performing stair ascent with a step-by-step technique where the sound limb leads and the prosthetic limb follows passively.

In order to overcome the limitations of controlled damping devices, alternatives have been developed, but with limited commercial success to date. Most notably, the Power Knee (available from Össur Americas of Foothill Ranch, Calif.) actuates the knee with a direct drive motor. A similar concept, with more sophisticated control, has been described recently. Direct drive devices consume far more electrical power than controlled dampers, which limits their applicability. It has been shown that series elastic actuators can dramatically reduce the power requirements. These actuators allow some of the knee function to be delivered by passive springs, and the control timing can be such that the motor mainly moves when unloaded.

In most cyclic activities, such as walking, running, and a stand-sit-stand sequence, no net positive work is required at the knee, which suggests that a motor may not be needed. There are, however, alternating phases of negative and positive work. Therefore, energy must be stored during periods of negative work, rather than dissipated with a damper, and the stored energy must be released later when positive work is needed. A stiff knee extensor spring, such as in the XT9 (available from SymBiotechs USA of Saratoga Springs, Utah) provides functional energy storage and release in stance-only activities, but is not suitable for walking where the spring must be disengaged during the swing phase. Although large reductions in metabolic cost were reported in test subjects, a disengageable-spring device never appears to have been commercialized. It may be that the passive mechanism to control the stance-swing transitions was not sufficiently safe against buckling, or too specialized to allow activities other than walking.

SUMMARY OF THE INVENTION

In an embodiment of the present invention, an energy-storing prosthetic knee is described. An upper leg structure is configured to attach to a socket for a transfemorally amputated residual limb. A lower leg structure is hingedly connected to the upper leg structure and is configured to attach to a lower limb prosthesis. The lower and upper leg structures move pivotally relative to one another during a gait cycle characterized by a plurality of gait periods. A fluid actuator has high and low pressure sides and is operatively connected to the upper and lower leg structures such that relative pivotal movement of the upper and lower leg structures causes a fluid to flow in a predetermined manner within the fluid actuator. At least two controllable variable fluid flow resisting devices, an accumulator, and a control system are also provided. The control system is configured to control first and second controllable variable fluid flow resisting devices to store, in the accumulator, fluid energy caused by fluid flow within the fluid actuator during gait periods of positive energy, release fluid energy to the fluid flow within the fluid actuator during gait periods of negative energy, and vary resistance to flow between the high and low pressure sides of the actuator during non-energy storing and release gait periods. The control system controls action of the first and second controllable variable fluid flow resisting devices in coordination with action of the accumulator. The control system is actuable to cause storage of the fluid energy for a predetermined length of time and release of the fluid energy at a predetermined time during the gait cycle. Both the storage and release of the fluid energy are variable by action of the control system without physical modification of other components of the prosthetic knee.

In an embodiment of the present invention, an energy-storing prosthetic knee is described. An upper leg structure is configured to attach to a socket for a transfemorally amputated residual limb. A lower leg structure is hingedly connected to the upper leg structure and is configured to attach to a lower limb prosthesis. The lower and upper leg structures move pivotally relative to one another during a gait cycle characterized by a plurality of gait periods. A fluid actuator has high and low pressure sides and is operatively connected to the upper and lower leg structures such that relative pivotal movement of the upper and lower leg structures causes a fluid to flow in a predetermined manner within the fluid actuator. At least two controllable variable fluid flow resisting devices, an accumulator; and a control system are provided. The control system is configured to control first and second controllable variable fluid flow resisting devices to store, in the accumulator, fluid energy caused by fluid flow within the fluid actuator during gait periods of positive energy, release fluid energy to the fluid flow within the fluid actuator during gait periods of negative energy, and vary resistance to flow between the high and low pressure sides of the actuator during non-energy storing and release gait periods. The control system controls action of the first and second controllable variable fluid flow resisting devices in coordination with action of the accumulator. The control system is actuable to cause storage of the fluid energy for a predetermined length of time and release of the fluid energy at a predetermined time during the gait cycle. Both the storage and release of the fluid energy are variable by action of the control system without physical modification of other components of the prosthetic knee.

BRIEF DESCRIPTION OF THE DRAWINGS

For a better understanding of the invention, reference may be made to the accompanying drawings, in which:

FIG. 12A is a partial front view of a prosthetic knee including the embodiment of FIG. 1;

FIG. 12B is a partial rear view of a prosthetic knee including the embodiment of FIG. 1.

DESCRIPTION OF EMBODIMENTS

Figure 1:
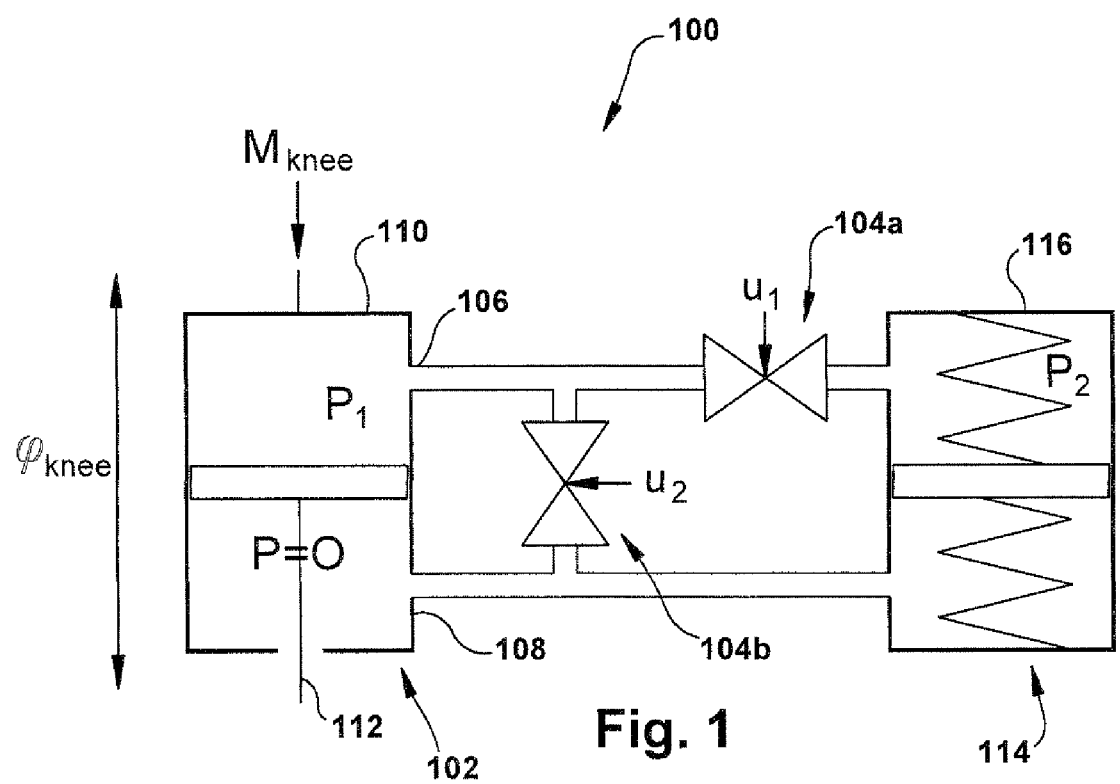
FIG. 1 is a schematic view of the present invention.

In accordance with the present invention, FIG. 1 schematically depicts a portion of an apparatus for asserting a transfemoral amputee with lower limb-involving user tasks. Here, the apparatus includes an energy-storing prosthetic knee 100, which stores energy during times of negative power in the amputee's gait cycle (characterized by a plurality of gait periods) and releases the energy as positive power to assist at a later time in the gait cycle. The operation and configuration of the prosthetic knee 100 will be described herein as being fluid-powered (e.g., hydraulic and/or pneumatic), but any suitable power scheme (e.g., electric, mechanical, spring-powered, rheological, or any other suitable type) could be used for a particular application of the present invention.

The prosthetic knee 100 includes at least one actuator 102, controlled by at least two controllable variable fluid flow resisting devices, shown and described herein as fluid valves 104a and 104b. The valves 104 may be any combination of relatively high- and relatively low-pressure valves, and may be controlled in any desired manner. The actuator 102 has high and low pressure sides 106 and 108, respectively. The actuator 102 is configured for operative connection to upper and lower leg structures such that relative pivotal movement of the upper and lower leg structures causes a fluid to flow in a predetermined manner within the actuator, as discussed below. For example, an upper leg structure may be connected to a cylinder 110 of the actuator 102 and a lower leg structure may be connected to a piston 112 of the actuator. The actuator 102 may be linear, rotary, or any other type and may be readily selected for a particular application of the present invention by one of ordinary skill in the art, based on any desirable factors. For example, a linear actuator may fit better, mechanically speaking, into the form factor of a particular prosthetic knee 100 and have better anti-leakage results, while a rotary actuator may help reduce shaft seal blowout and force transmission angle problems.

First valve 104a controls flow to an accumulator 114 (which may be spring-loaded, as shown) where energy can be stored, and second valve 104b bypasses the accumulator. When first valve 104a remains closed, and only second valve 104b is used for control, the prosthetic knee 100 may bear some mechanical and operational similarities to a controlled damper device, as known in the art of transfemoral prostheses. The accumulator 114 may be of any suitable type, including a force-biased accumulator, and may include a spring feature 116 comprising one or more linear or nonlinear springs.

Optionally, the accumulator 114 may be configured in any suitable manner for variable compliance behaviour, which may change during an amputee's gait cycle or which may stay constant through a plurality of gait cycles, depending on the desired use characteristics of the prosthetic knee 100. For example, the spring feature 116 may have a single variable-compliance spring and/or a nested plurality of springs to provide the desired variable compliance characteristics to the accumulator 114. Alternatively or additionally, a nonlinear accumulator 114, a plurality of any type of accumulators and valves 104, or another active control mechanism (which may or may not include an accumulator), could be provided to obtain desired variable compliance results in the system of the prosthetic knee 100.

Figure 2:
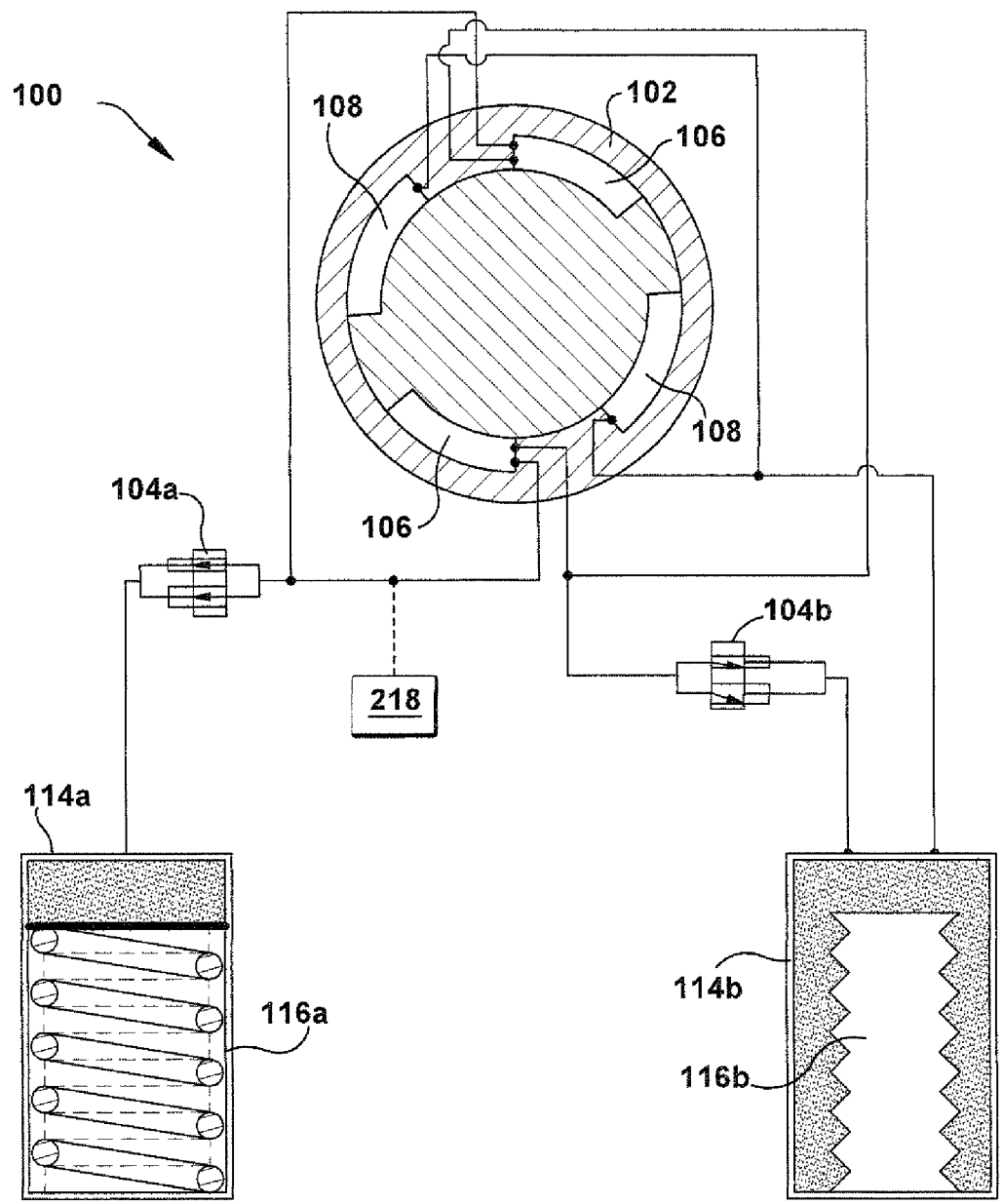
FIG. 2 is a schematic view of a hydraulic system according to a first arrangement of the embodiment of FIG. 1.

FIG. 2 schematically depicts the prosthetic knee 100 in a first configuration. The prosthetic knee 100 is configured to "harvest" (via a fluid energy loop) and store input energy from the amputee during certain, positive energy gait periods of the amputee's gait cycle, and then to release the stored energy to the amputee to assist or boost the power available to the amputee during other, negative energy gait periods of the amputee's gait cycle. In other words, a control system 218 is shown schematically as being operatively connected to other components of the prosthetic knee 100 in FIG. 2; the control system may be of any suitable type and will normally be operatively connected (in a wired or wireless manner) to a plurality of the other components of the prosthetic knee, but these connections are omitted in the Figures for clarity.

The control system 218 is configured to control the first and second valves 104a and 104b to store, in the accumulator 114, fluid energy caused by fluid flow within the fluid actuator 102 during gait periods of positive energy. The fluid actuator 102 obtains this "excess" fluid energy through transformation of applied forces from the amputee into fluid energy. For example, during the transition from a heel strike gait period to a midstance gait period, the amputee's weight may urge the piston 112 deeper into the cylinder 110 of a linear actuator 102 to produce higher pressure within the fluid chamber of the actuator 102 and thus perform pumping work.

The control system 218 is also configured to control the first and second valves 104a and 104b to release from the accumulator 114 previously stored fluid energy to the fluid flow within the fluid actuator 102 during gait periods of negative energy. For example, during a pre-swing gait period, the fluid energy could be routed to the fluid chamber of the actuator 102 to help force the piston 112 outward from the cylinder 110 of a linear actuator 102 and thus help the amputee position for toe-off and swing initiation with a power boost.

The control system 218 also may vary resistance to flow between the high and lower pressure sides 106 and 108 of the actuator 102 during non-energy storing and/or release gait periods. In other words, the control system 218 could control action of the first and second valves 104a (high pressure, in FIG. 2) and 104b (low pressure, in FIG. 2) in coordination with action of the accumulator 114 during various gait periods of the gait cycle to at least partially regulate fluid flow through the prosthetic knee 100 and thereby achieve desired force response results for the amputee when the gait period is not energy-storing or -releasing. During these gait periods of neutral energy, it is anticipated that (under most circumstances) both the first and second valves 104a and 104b would only be simultaneously open if the accumulator 114 had gotten overcharged, such as during the transition from a heavy work task to a light work task. If the accumulator 114 is empty, the first valve 104a can be open during certain gait periods (e.g., free swing phase) without significant effect upon the functioning of the prosthetic knee 100 because the input pressures will be too low to drive the accumulator 114. In such event, the operation of the second valve 104b will not be impeded.

The control system 218 is configured and actuable to cause storage of fluid energy (e.g., in the accumulator 114) for a predetermined length of time and release of the fluid energy (e.g., to the actuator 102) at a predetermined time during the gait cycle. Both the storage and the release of the fluid energy are variable by action of the control system 218 without physical modification of other components of the prosthetic knee 100. That is, the flow of the fluid through the components can be controlled independent of the gait period. If desired, even more fluid energy could be provided to the actuator 102, for example, during a positive energy gait period to stiffen the prosthetic knee 100. The fluid flow through the components, when controlled by the control system 218, does not rely upon when in the gait cycle the amputee creates pumping work or needs a power boost.

The control system 218 may control action of the first and second valves 104a and 104b in coordination with the gait of the amputee. The first and second valves 104a and 104b could be controlled, for example, to supplement a locomotive gait of the amputee (e.g., walking, jogging, running, climbing or descending stairs, climbing or descending an incline, or the like) or any other lower limb-involving user task, such as, but not limited to, sitting down, standing up, squatting, or the like. The first and second valves 104a and 104b could be controlled, as well, to abruptly begin or end transfer of fluid energy under a rapid-response control system 218 scheme which facilitates stability and effective assistance via the prosthetic knee 100 during an irregular gait cycle or other user task.

Optionally, rather than a proportional fluid valve 104, a plurality of poppet fluid valves (not shown) may be arranged in parallel with each other to assist with control of the prosthetic knee 100, each fluid valve having a different series resistance. In this situation, the control system 218 may be a tunable control system which controls the plurality of poppet fluid valves in different actuation combinations to provide a plurality of response modes, with each response mode bearing a direct relationship to a desired force response of the prosthetic knee 100 for a particular user task.

Any desired sensors, programming interfaces, or other components (not shown), along with suitable control programs, could be included in the prosthetic knee 100 to aid the control system 218 in determining when to store fluid energy and release the stored energy. Optionally, the amputee and/or the amputee's prosthetist or other medical professional could configure the control system 218 to achieve desired energy transfer results, on either a one-time/occasional basis (e.g., an initial personalization programming session) or an ongoing basis (e.g., a "switch to running mode" button). That is, the control system 218 may be tunable and have a plurality of predetermined (by the manufacturer, supplier, medical professional, and/or consumer) response modes for operation. Each response mode may include tuned control of at least one of a starting accumulator 114 pressure, the pressure/displacement variance of the accumulator, valve resistance to flow, or any other suitable control factors of the prosthetic knee 100.

The control system 218 may also include preprogrammed or machine learning features that allow for automatic sensing of an anticipated response mode and appropriate control of the prosthetic knee 100 to provide "unconscious" or non-user-prompted switching between response modes as the amputee moves between user tasks. It is contemplated that the control system 218 may include selectable predetermined response modes and/or custom-created (optionally with reference to historical data for that amputee) response modes which may be called up manually and/or automatically during use of the prosthetic knee 100 by the amputee. Given sufficiently sophisticated sensing, control algorithms, response mode data, and prosthetic knee 100 construction, an amputee may even be able to experience performance from the prosthetic knee 100 that mimics that of a native knee.

Each response mode is contemplated as bearing a direct relationship to a desired force response of the prosthetic knee 100 for a particular user task. For instance, and as shown in FIG. 1, first valve 104a controls the energy storage and release. During a transition from standing to sitting, second valve 104b should be mostly closed and first valve 104a should be open to let fluid flow into the accumulator 114. While the amputee is sitting, first valve 104a may remain closed to keep the spring feature 116 in its deformed state and second valve 104b can be opened to relax the limb. When the amputee is ready to stand up, second valve 104b should close, and first valve 104a should modulate open and let the accumulator 114 push fluid back into the actuator 102 at a controlled rate to generate active knee extension. For level walking, the desired valve control will likely be such that second valve 104b is mostly modulated through appropriate open states during the swing phase, and closed during stance, while first valve 104a should be cycling open, closed, and then open again as appropriate to gait period during stance to allow energy storage and release.

The control system 218 may be programmed to carry out, through control of the first and second valves 104a and 104b or any other components of the prosthetic knee 100, an energy receipt-storage-release cycle that bears a predetermined and supplemental relationship to a gait energy requirement cycle (or any user task energy requirement cycle) of a transfemoral amputee, such as regulating and/or supplementing a locomotive gait of the amputee. The energy receipt-storage-release cycle may be selectively variable through actuation of the control system 218, without structural change to remaining components of the prosthetic limb. That is, unlike prior art systems where, for example, a spring needed to be replaced by a different spring to achieve different force response results, the present invention allows for a high degree of customizability and many operational mode options to provide the amputee with options for prosthetic control that can help improve the amputee's biomechanics and even her quality of life.

As shown in FIG. 2, an example configuration of a prosthetic knee 100 includes two accumulators, a high pressure accumulator 114a and a low pressure accumulator 114b, along with corresponding first and second valves 104a and 104b, respectively. An example of "high pressure" in some systems may be in the range of 500-2000 psig, while "low pressure" could be in the range of 3-15 psig. Optionally, the first and second valves 104a and 104b may be high-pressure and low-pressure valves, respectively, as well. (Currently, existing prosthetic knees often have a low pressure accumulator to accommodate fluid losses over time or volume changes with temperature.)

Here, the low pressure accumulator 114b, when present, may be helpful to provide (1) a reference pressure slightly above ambient pressure and thereby help the hydraulic system to avoid internal vacuum, and/or (2) variable volume capacity in the hydraulic system to accommodate charging and discharging of the high pressure accumulator 114a. The high pressure accumulator 114a and associated high-pressure valve 104a described herein have an energy storage and return function.

A dynamic computational model of the proposed device will now be discussed with reference to FIGS. 3-5, and open loop desired control methods used to examine the feasibility of replicating able-bodied function during walking, running, and sitting/standing motion using the prosthetic knee 100.

Kinematic and kinetic data for three subjects were collected using an 8-camera Eagle/EVaRT system (available from Motion Analysis Corporation of Santa Rosa, Calif.), and AMTI model OR6-5 force plates at 60 samples per second. Three able-bodied subjects (88±23 kg, 170±11 cm) performed one trial each of normal walking (1.33±0.18 m s$^{-1}$), slow running (2.72±0.37 ms$^{-1}$), and a sit-stand-sit cycle (3.53±1.15 s). Data from the right lower extremity were processed by Orthotrak 6.6 (available from Motion Analysis Corporation of Santa Rosa, Calif.) into joint angles and joint moments for a full cycle of each activity. All data were low-pass filtered bidirectionally with a 6 Hz 2$^{nd}$ order Butterworth filter.

A computational model of the hydraulic system for a prosthetic knee 100 having a rotary actuator 102 was developed. The rotary actuator 102 establishes relationships between actuator 102 pressure $P_1$ and knee joint moment M:

$$M = RAP_1 \quad (1)$$

where R is the radius of the actuator and A is the vane area. The relationship between knee angular velocity $\dot{\phi}$ and the flows $v_1$ and $v_2$ through the parallel valves (104a and 104b in FIG. 1) is:

$$v_1 + v_2 = RA\dot{\phi} \quad (2)$$

The spring-loaded accumulator 114 was modeled as a linear spring:

$$\dot{P}_2 = kv_1 \quad (3)$$

Each of the two valves 104a and 104b was modeled using a quadratic (turbulent flow) relationship between pressure drop $\Delta P$ and flow rate v:

$$v = u(t)C\sqrt{\Delta P} \quad (4)$$

where C is the valve constant and u(t) is a dimensionless valve control signal between zero (closed) and one (open). (It should be understood that other, potentially non-quadratic relationships, such as a power law of the type $y = ax^{b,cd}$, may be used to help model various hardware configurations and testing schemes.) Each valve and associated tubing was assumed to have an additional pressure drop $\Delta P = Bv$ due to viscous drag.

The entire system of the prosthetic knee 100 shown in FIG. 1 may now be represented by a system of four differential-algebraic equations:

$$\dot{P}_2 - kv_1 = 0 \quad (5)$$
$$u_1(t)^2 C_1^2 \left( P_2 - \frac{M}{RA} - B_1 v_1 \right) - v_1|v_1| = 0$$
$$RA\dot{\phi} - v_1 - v_2 = 0$$
$$u_2(t)^2 C_2^2 \left( \frac{M}{RA} + B_2 v_2 \right) + v_2 + |v_2| = 0$$

When valve control inputs $u_1(t)$ and $u_2(t)$ and all model parameters are given, there are five unknowns which are functions of time: $P_2$, M, $\dot{\phi}$, and the two flow variables $v_1$ and $v_2$. One unknown can be eliminated by prescribing either $\phi(t)$ or M(t), or both unknowns may be kept, and the model used as a dynamic relationship between knee angle and knee moment. Here, the latter will be chosen. When solving the model, periodic boundary conditions are used for the differential equation, to ensure that the accumulator 114 has not generated or absorbed net energy during the entire movement cycle. In other words, it is anticipated that the movement can be repeated indefinitely. The accumulator 114 stiffness k will be optimized as described below. The other design parameters were given constant values listed in Table 1, based on the anticipated size of the actuator 102 and other hydraulic components.

TABLE 1

Assumed design parameters for the hydraulic hardware.

| Parameter | Value | Description |
|---|---|---|
| R · A | 7.30 cm$^3$ | Volume of rotary hydraulic cylinder |
| $C_1, C_2$ | 30 cm$^3$ s$^{-1}$ MPa$^{-0.5}$ | Valve constants |
| $B_1, B_2$ | 0.01 MPa s cm$^{-3}$ | Drag coefficient for valves and associated tubing |

In order to find the accumulator 114 stiffness and valve control profiles that best reproduce able-bodied knee function, the following desirability criterion was defined:

$$F(\cdot) = \frac{w_1}{T} \int_0^T \left(\frac{\phi(t) - \phi_0(t)}{\sigma_\phi}\right)^2 + \tag{6}$$
$$\frac{w_2}{T} \int_0^T \left(\frac{M(t) - M_0(t)}{\sigma_M}\right)^2 + \frac{w_3}{T} \int_0^T (\overline{u}_1(t)^2 + \overline{u}_2(t)^2)^2,$$

where $\phi(t)$ and $M(t)$ are the joint angle and joint moment generated by the model, and $\phi_0(t)$ and $M_0(t)$ are data from an able-bodied subject performing the desired activity of duration T. The first two terms represent tracking of able-bodied data, made dimensionless by normalizing to experimental standard deviations, and the third term represents the cost of operating the valves 104a and 104b. This cost was assumed to be related to the second derivative of valve position and was added to encourage smooth and energy efficient control profiles. The weight factors were $w_1=w_2=1$ and $w_3=0.1$. Since only one trial of data was available for each subject in each activity, the standard deviations were arbitrarily set to $\sigma_Q=5°$ and $\sigma_M=5$ Nm. These weights and coefficients were arbitrary and selected because these produced good results. Results were, however, not sensitive to these choices.

The open loop desired control problem can now be formulated as follows: find periodic functions $u_1(t)$, $u_2(t)$, $P_2(t)$, $M(t)$, $\phi(t)$, and stiffness k which satisfy equations (5) and minimize the cost function (6). The problem was solved by direct collocation, in which the unknown functions were time-discretized using the trapezoidal rule for differential equation (5a). This general approach has been applied to desired control of human gait by previous researchers. The constrained large scale optimization problem, resulting from temporal discretization, was implemented in Matlab (available from Mathworks of Natick, Mass.), and solved by the SNOPT solver (available from Tomlab Optimizaiton of Seattle, Wash.). To prevent numerical singularity, a lower bound of 0.001 was imposed on the controls u(t), i.e. valves could not be perfectly closed. This bound is low enough to have no noticeable effect on the solution, only on the ability of the numerical methods to find the solution. Solutions were first obtained on a coarse mesh of 20 time points, and then successively refined until the movement cycle was sampled at the 60 Hz sampling rate at which data were collected.

For each of the three movements in each of the three subjects, three desired control problems were solved. First, the full optimization problem in which accumulator stiffness and both valve controls were all calculated. Second, the optimization was performed with a fixed accumulator 114 stiffness of 5 MPa cm$^{-3}$. This represents the situation where the same accumulator 114 is used for multiple movements and/or subjects. Third, the optimization was performed with first valve 104a always closed and control only in second valve 104b, which is equivalent to a conventional controlled damper style prosthetic knee.

Figure 3:
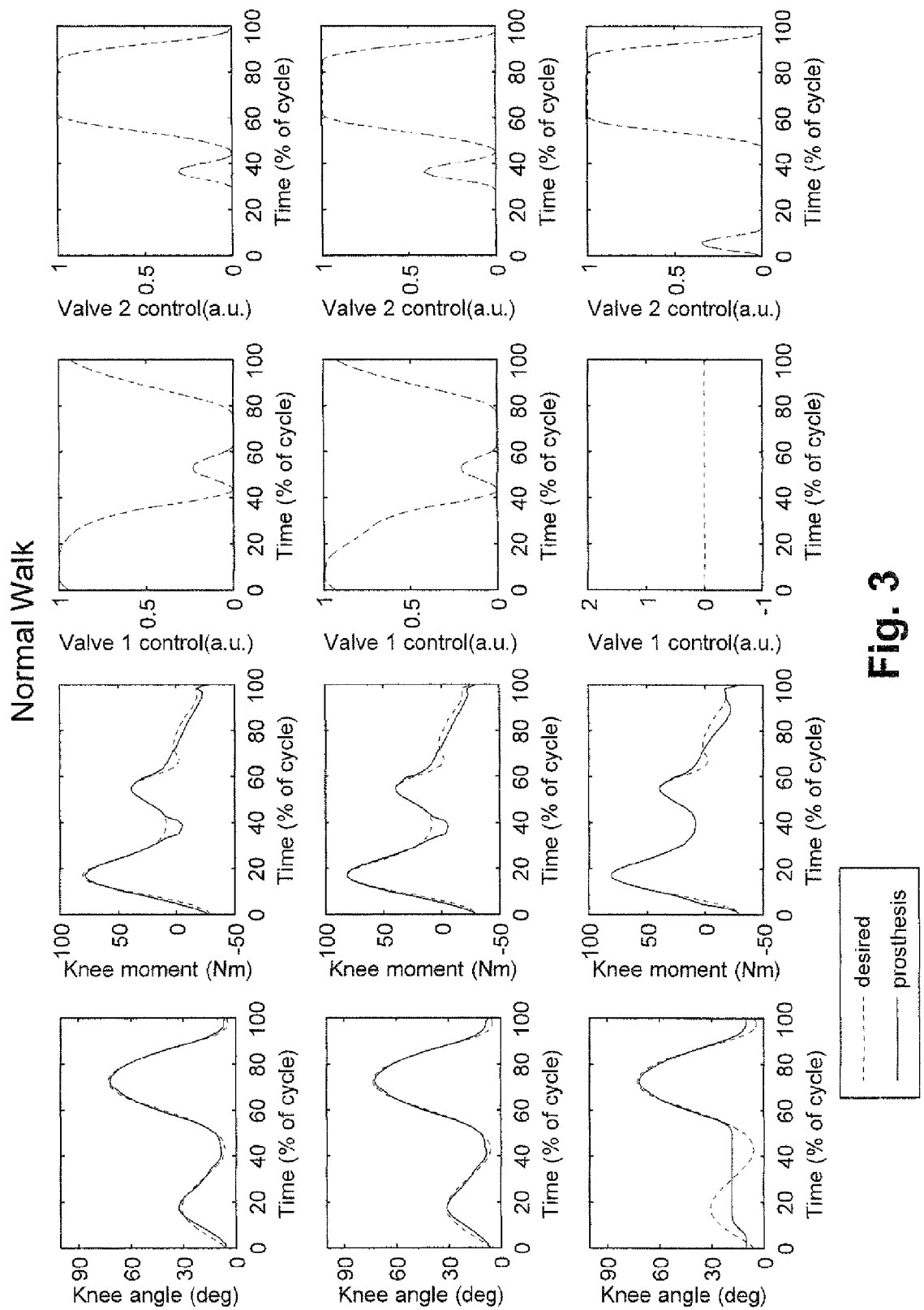
FIG. 3 depicts various response charts for optional configurations of the embodiment of FIG. 1 during a walking user task.

Desired control solutions for normal walking in subject 1 are shown in FIG. 3. After some optimization work, the prosthetic knee model was able to reproduce the angle-moment-time relationships of able-bodied gait almost perfectly. In order to do this, second valve 104b was mostly closed during stance and modulated open during swing, similar to typical controlled damper knees. Additionally, first valve 104a is opened in late swing and early stance phase for desired energy storage and return. When first valve 104a remains closed, as in a controlled damper device, a stiff knee gait can be accomplished. In summary, FIG. 3 shows desired control solutions for normal walk (subject 1). Top row: full optimization which found a desired accumulator 114 stiffness of 4.15 MPa cm$^{-3}$. Middle row: optimization in which accumulator 114 stiffness was fixed at 5.0 MPa cm$^{-3}$. Bottom row: optimization in which first valve 104a was kept closed. Valves 104 are open when control signal is one, and closed when control signal is zero.

Figure 4:
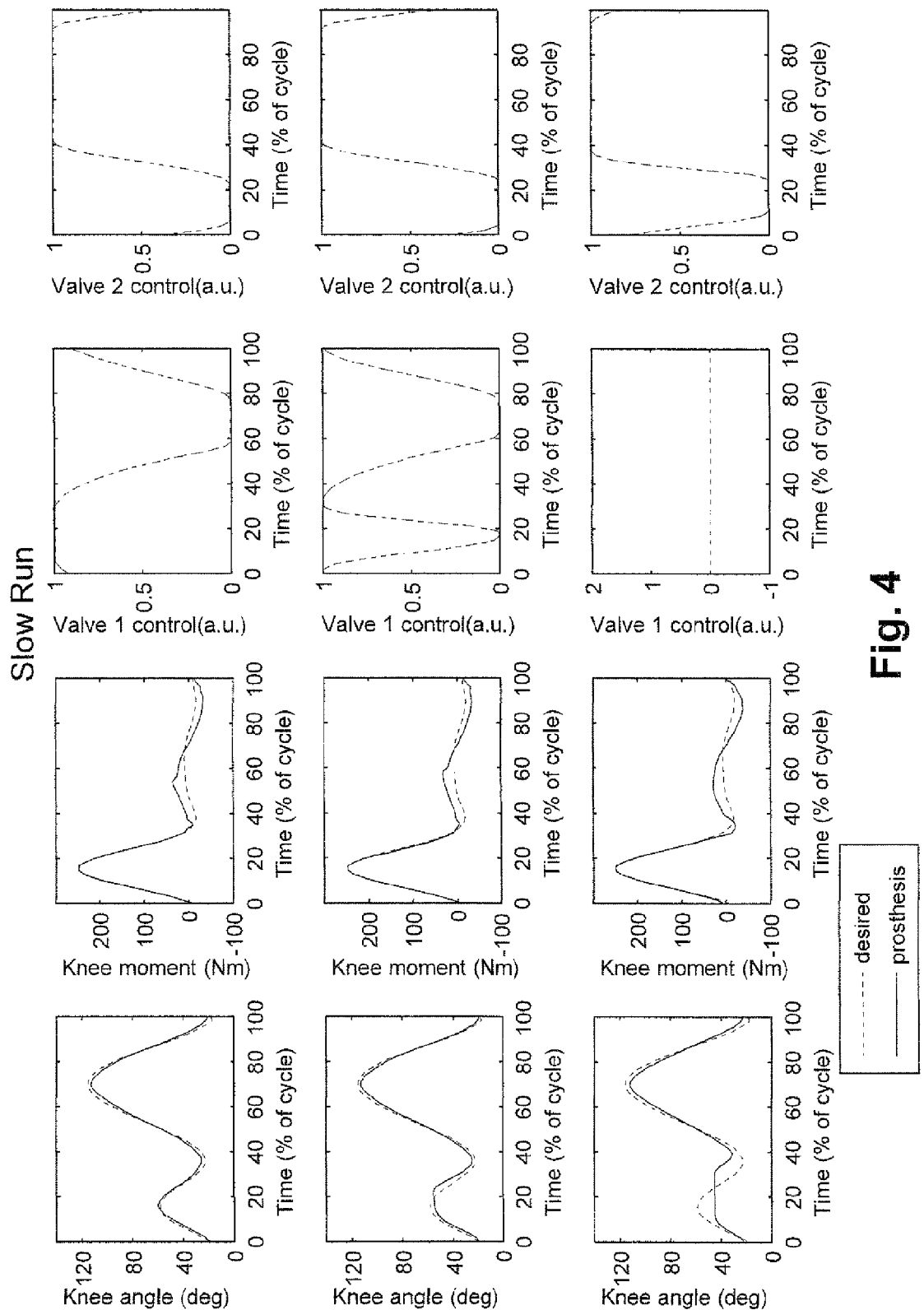
FIG. 4 depicts various response charts for optional configurations of the embodiment of FIG. 1 during a slow run user task.

Desired control solutions for slow running in subject 1 are shown in FIG. 4. As in walking, the model of the prosthetic knee 100 was able to fit closely to the able-bodied gait data with a full optimization. The desired accumulator 114 stiffness, however, was larger than in walking and performance was slightly compromised when stiffness was set at a value of 5 MPa cm$^{-3}$, which is desired for walking. In order to prevent excessive knee flexion with the too-soft accumulator 114, first valve 104a had to be closed briefly during the stance phase, which locked the knee angle for that period of time.

In summary, FIG. 4 shows desired control solutions for slow run (subject 1). Top row: full optimization which found a desired accumulator 114 stiffness of 7.64 MPa cm$^{-3}$. Middle row: optimization in which accumulator 114 stiffness was fixed at 5.0 MPa cm$^{-3}$. Bottom row: optimization in which first valve 104a was kept closed.

FIG. 4 shows a typical desired control solution for a sit-stand-sit cycle. As hypothesized, first valve 104a opens to absorb energy during sitting down (50-80% of cycle), remains closed during sitting (80-10%), and then opens again to assist the standing up (10-40%). The desired controls were continuous and produced smooth transitions between these phases. Desired accumulator 114 stiffness was much lower than for walking and running. When a walking stiffness was used to perform the sit-stand-sit task, it was difficult to generate the required motion and torque at the same time.

Figure 5:
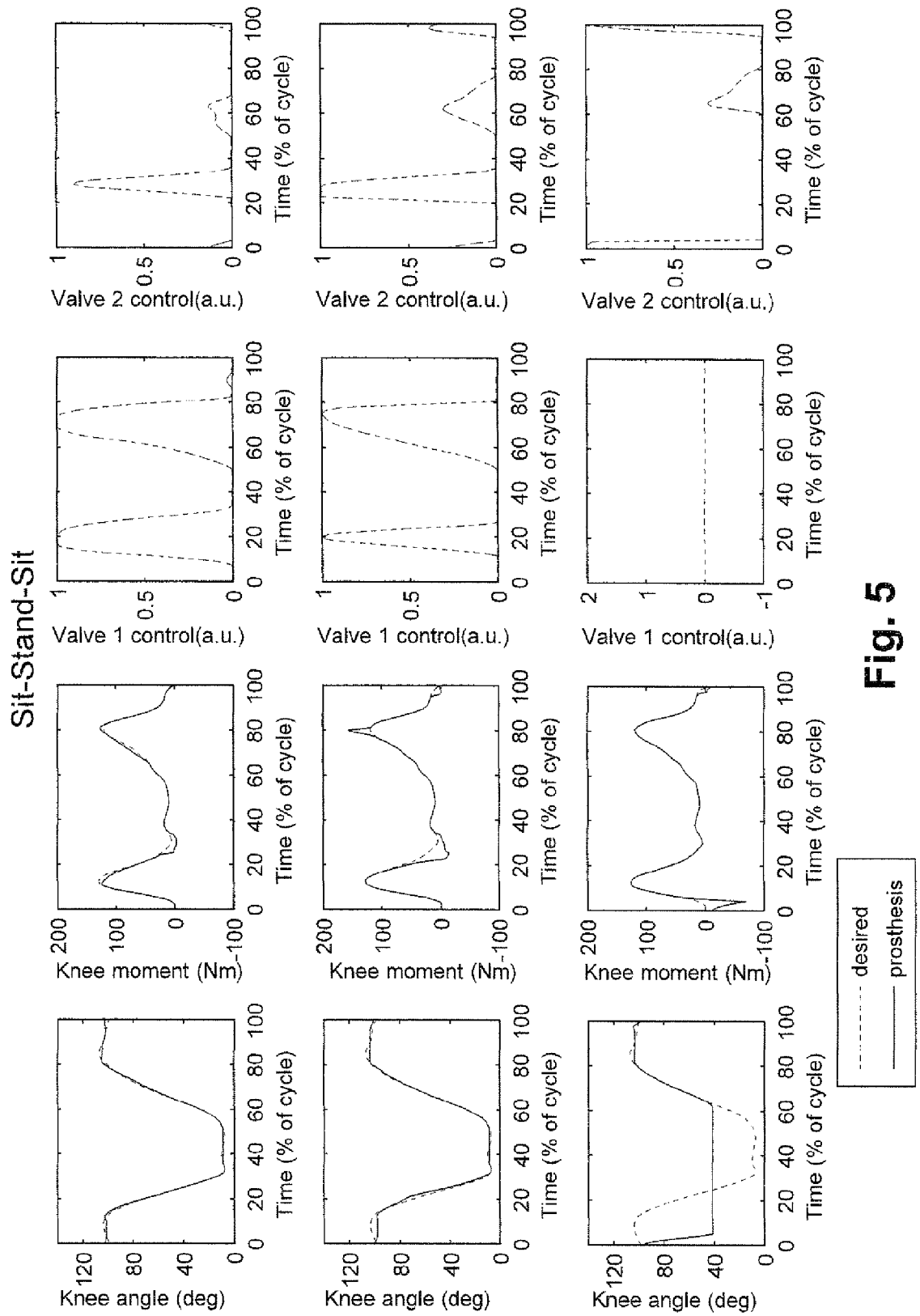
FIG. 5 depicts various response charts for optional configurations of the embodiment of FIG. 1 during a sitting/standing user task.

In summary, FIG. 5 shows desired control solutions for slow run (subject 1). Top row: full optimization which found a desired accumulator 114 stiffness of 1.71 MPa cm$^{-3}$. Middle row: optimization in which accumulator 114 stiffness was fixed at 5.0 MPa cm$^{-3}$. Bottom row: optimization in which first valve 104a was kept closed.

Results were consistent across subjects, as shown in Table 2, below.

TABLE 2

Desired accumulator stiffness and RMS tracking errors for the three movement conditons (mean and SD of 3 subjects). In each movement condition, three desired control problems were solved: a full optimization, an optimization in which accumulator stiffness was not optimized but fixed at 5.0 MPa cm$^{-3}$, and an optimization in which first valve 104a remained closed to mimic a conventional controlled damper device.

| | Optimization Type | RMS angle error (deg) | RMS moment error (Nm) | Desired accumulator stiffness (MPa cm$^{-3}$) |
|---|---|---|---|---|
| NORMAL WALK | full optimization | 1.7 ± 0.2 | 4.9 ± 0.7 | 5.0 ± 1.0 |
| | k = 5.0 MPa cm$^{-3}$ | 1.9 ± 0.4 | 4.9 ± 0.7 | N/A |
| | first valve closed | 5.3 ± 2.3 | 4.9 ± 0.7 | N/A |

TABLE 2-continued

Desired accumulator stiffness and RMS tracking errors for the three movement conditons (mean and SD of 3 subjects). In each movement condition, three desired control problems were solved: a full optimization, an optimization in which accumulator stiffness was not optimized but fixed at 5.0 MPa cm$^{-3}$, and an optimization in which first valve 104a remained closed to mimic a conventional controlled damper device.

|  | Optimization Type | RMS angle error (deg) | RMS moment error (Nm) | Desired accumulator stiffness (MPa cm$^{-3}$) |
|---|---|---|---|---|
| SLOW RUN | full optimization | 2.1 ± 0.5 | 10.0 ± 3.9 | 8.5 ± 1.1 |
|  | k = 5.0 MPa cm$^{-3}$ | 3.1 ± 0.5 | 10.1 ± 3.4 | N/A |
|  | first valve closed | 5.4 ± 1.6 | 10.7 ± 4.4 | N/A |
| SIT-STAND-SIT | full optimization | 1.2 ± 0.3 | 4.9 ± 1.3 | 1.2 ± 0.4 |
|  | k = 5.0 MPa cm$^{-3}$ | 3.6 ± 1.1 | 12.3 ± 2.8 | N/A |
|  | first valve closed | 24.7 ± 7.2 | 9.5 ± 2.1 | N/A |

With full optimization, tracking of able-bodied data was generally worst during running. Nevertheless, some stance phase flexion-extension was observed. Desired accumulator 114 stiffness varied between movements (Table 2) and was highly correlated to subject weight.

Open-loop desired control simulations of an energy-storing prosthetic knee 100 are presented. Such simulations can guide the hardware design (accumulator stiffness, valve constants) of the proposed device, as well as the development of a control system 218. It should be noted, however, that the open loop control patterns might not be able to be directly applied in a clinical device. Sensor-based controls could be developed from these desired patterns, which will allow amputees to control the cadence and amplitude of their movements. Adaptive controllers with state-machine techniques may be developed, as has previously been done for controlled dampers.

A limitation of the above approach is that human body dynamics was not considered. When tracking errors are small, dynamic consistency is expected because results remain close to an observed able-bodied human performance. When tracking errors are large, however, results might no longer be consistent with a possible human performance, and results might be interpreted as an indication that replication of able-bodied function may be difficult. Such results occurred, for example, when the sit-stand-sit cycle was attempted with an accumulator 114 that was too stiff. It may be possible to perform the task in a different way, and this can be simulated, for example, with a model that includes full body dynamics. Such a model may allow prediction of compensatory actions that may be helpful in performing the task to compensate for possible limitations in the prosthetic device.

When first valve 104a remained closed, such that the device functioned as a controlled damper, the optimizations showed less-than-full flexion-extension movement in the stance phase during walking and running. Desired control simulations presented here suggest that this is indeed one example of a gait that can be achieved with known variable-damper devices such as the Rheo Knee and C-Leg. The model also showed that a variable damper might not be wholly useful during a sit-stand-sit cycle. With the energy storing mechanism in use, more desirable performance was achieved by the model in all three activities. This justifies further prototyping and human studies to compare this concept to controlled dampers, such as the Rheo Knee and C-Leg, when used by patients.

The simulations used preliminary estimates of the hardware design parameters (Table 1). One parameter of interest is the actuator 102 volume (R·A) which translates angles and moments into fluid flow and pressure. If this volume is changed, the desired valve controls will remain similar, and the accumulator stiffness may be scaled. The viscous drag coefficients B were assumed to be very small, and valve 104 coefficients C were assumed to be large, but realistic, because this gives the valves a relatively large amount of control over the fluid flow. As long as B remains small and C large, the desired valve 104 control profiles and accumulator stiffnesses are not sensitive to these assumptions.

The results herein show that performance may be better if the accumulator 114 stiffness is considered for each movement. While it is not practical to have a separate prosthetic knee 100 for each user task, variable stiffness may be possible with some hardware modifications. One option is to have two accumulators 114 in parallel, having different stiffnesses, and each controlled individually, such as by a separate valve 104. This will effectively give three different accumulator 114 stiffness profiles and these can be chosen such that they include the desired stiffnesses for sit-stand movements, for gait, and perhaps for running. Another option is to provide an accumulator 114 with a nonlinear pressure-volume relationship, such that the knee stiffness is decreased at large knee flexion angles. This may facilitate the sit-stand-sit cycle to be performed with the same accumulator 114 as the run and the walk.

While the energy-storing concept has good theoretical performance during walking, running, and standing up, there are other activities where the concept might not work in the same way. Upstairs walking and uphill walking, with able-bodied movement patterns, requires net positive work to be performed at the knee. It might be difficult to do this within one cyclic performance of those tasks, but might be easier to do this over a longer time period. During level gait, there is about 20 W of excess energy at the knee, some of which can be harvested into the accumulator 114, and then released in a controlled manner during activities that require net positive work. Another option is to have a small pump that charges the accumulator 114 over time, but this will require a source of energy.

The proposed energy-storing prosthetic knee 100 may help to provide near-normal function during a range of activities of daily living. The prosthetic knee 100 approaches the performance of a desired motor-driven joint while having the low power consumption of a controlled damper. Further work may be helpful to translate the open loop desired valve control profiles into a sensor-based controller.

Figure 6:
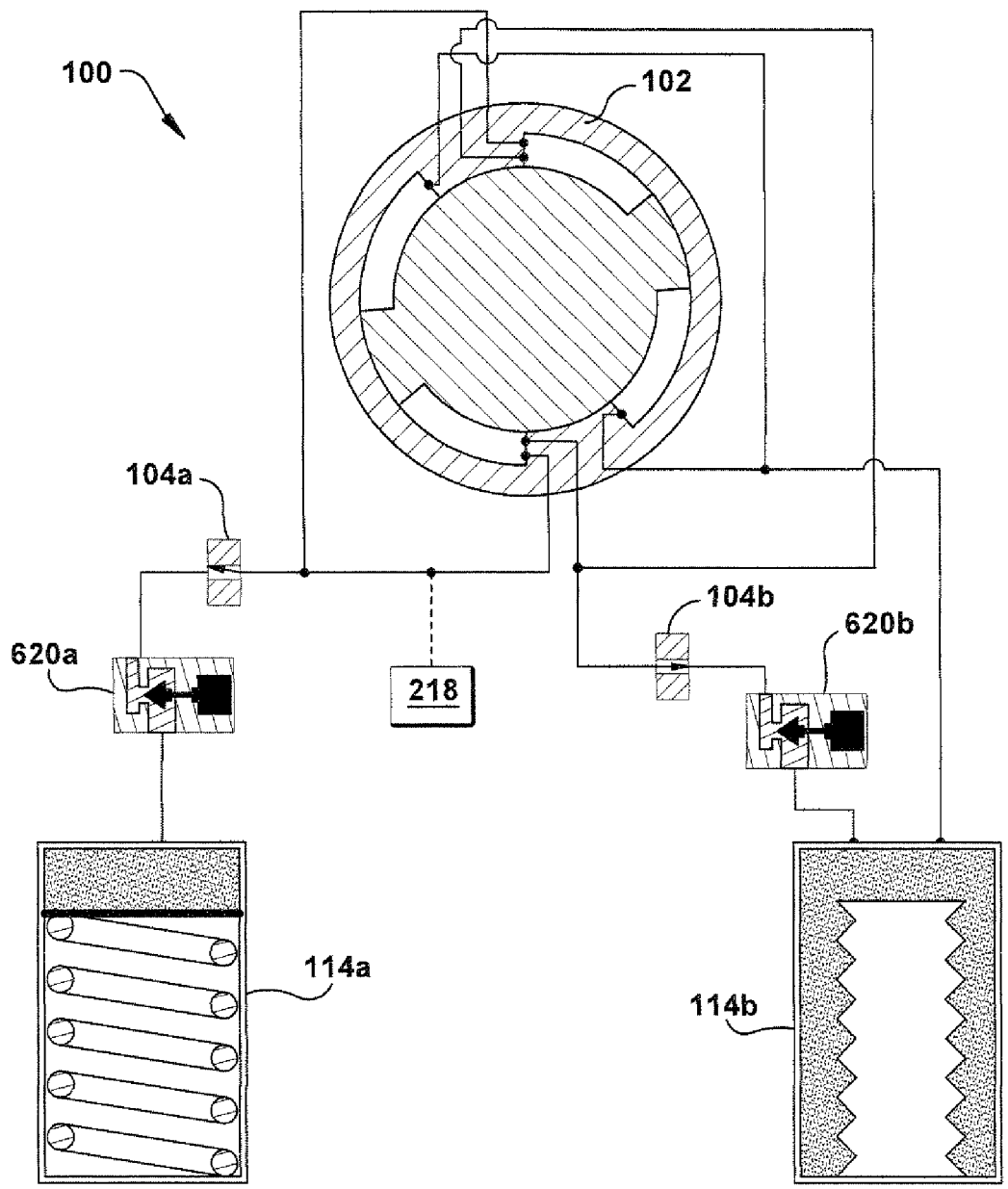
FIG. 6 is a schematic view of a hydraulic system according to a second arrangement of the embodiment of FIG. 1.

FIG. 6 depicts a prosthetic knee 100 similar to that shown in FIG. 2, having high- and low-pressure accumulators 114a and 114b, and which includes variable orifices 620 between the accumulators and the respective first and second valves 104a and 104b. The variable orifices 620, when present, may help to provide the prosthetic knee 100 with the functionality of a proportional valve 104 (such as those shown in FIG. 2) while using a simple poppet valve design for valve 104.

Figure 7A:
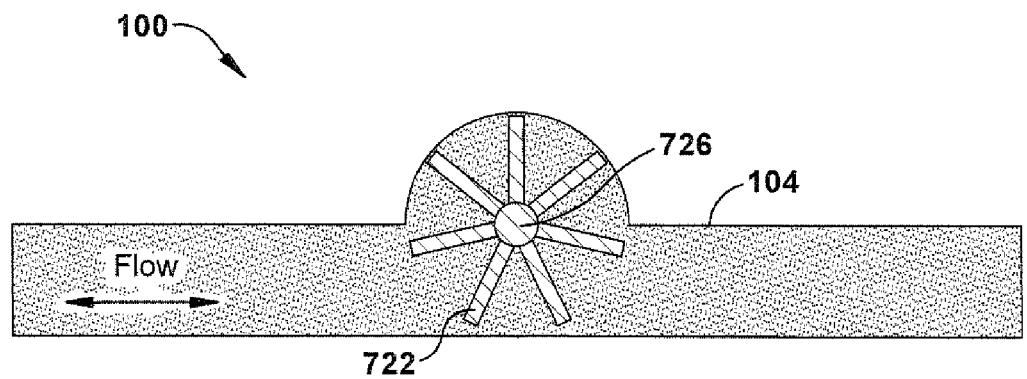
FIG. 7A is a partial schematic cutaway side view of a hydraulic component of the embodiment of FIG. 1.
Figure 7B:
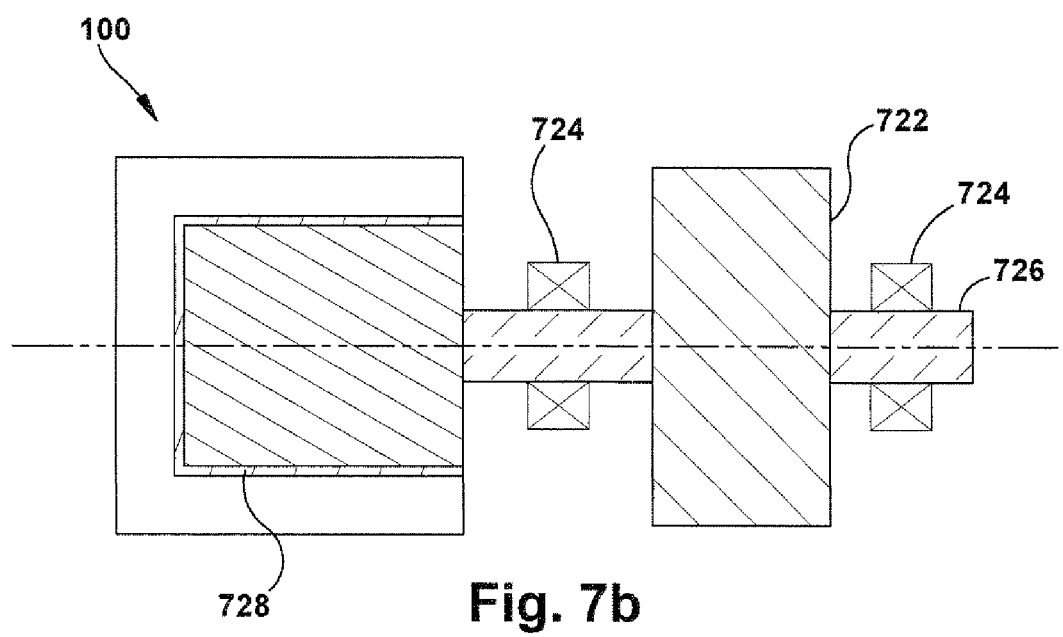
FIG. 7B is a partial schematic front view of a system including the component of FIG. 7A.

FIGS. 7A-7B depict an option for a proportional valve 104 substitute in which a paddlewheel 722 is the controllable variable fluid flow resisting device, and is placed in line as a restrictor with the fluid flow between the actuator 102 and accumulator 114. The ease of rotation of the paddlewheel 722 is used to decrease or increase resistance to fluid flow and thus control actuation of the prosthetic knee 100 features. As shown in FIG. 7B, the paddlewheel 722 may be supported by bearings 724 upon a shaft 726 for turning engagement with a torque device 728, which can be controlled by the control system 218 to vary the resistance of the paddlewheel 722 within the fluid flow.

Figure 8:
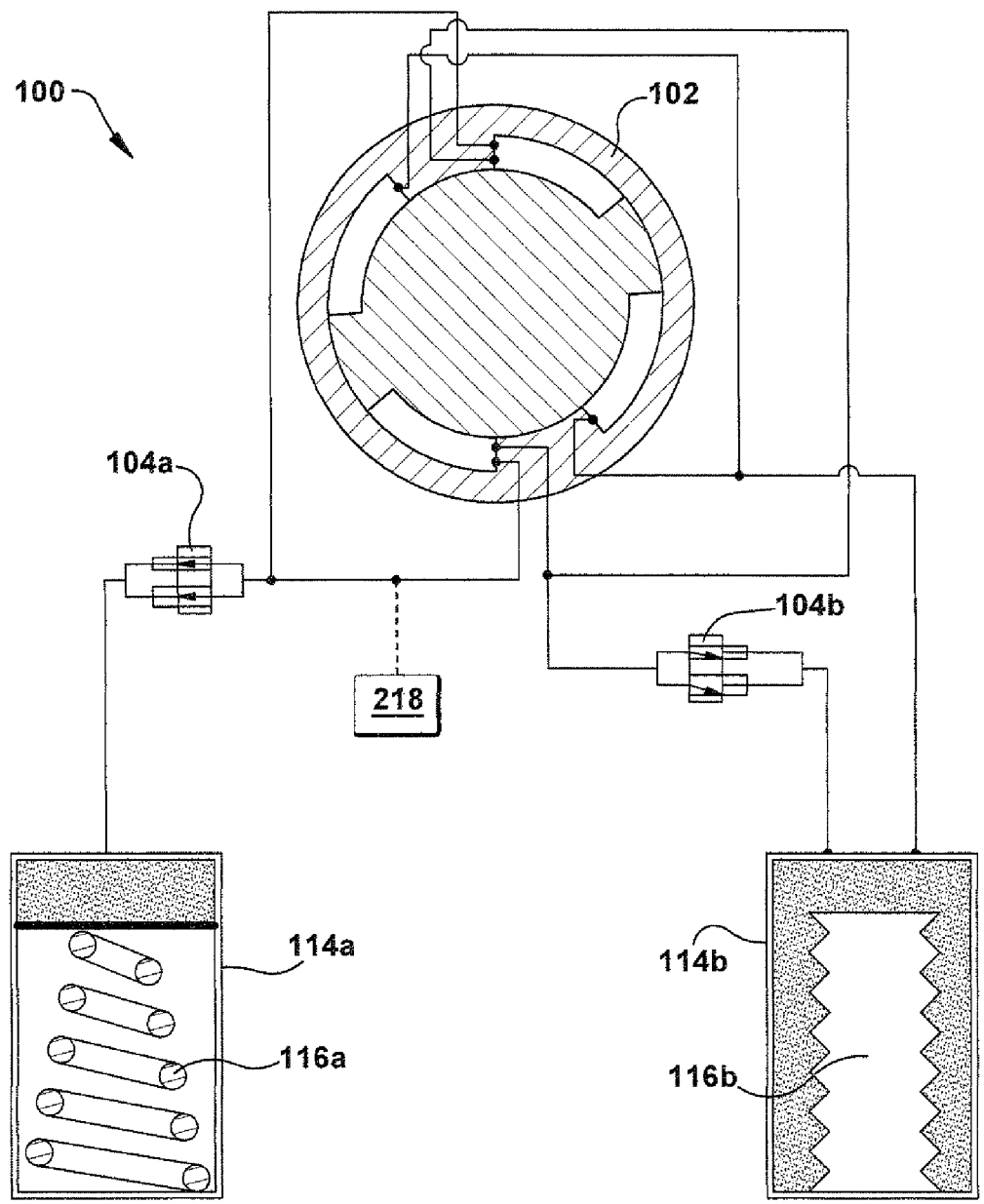
FIG. 8 is a schematic view of a hydraulic system according to a third arrangement of the embodiment of FIG. 1.

The prosthetic knee 100 shown in FIG. 8 is similar to that of FIG. 2, but having a non-linear spring feature 116a in the high-pressure accumulator 114a. By helping the accumulator 114a to charge to different fluid levels, the control system 218 can change the starting pressure and the compliance pattern of the accumulator to suit different gait conditions through use of the non-linear spring feature 116a. With a constant stiffness (linear spring) that is designed for walking, (low pressure) valve 104b will need to open during the sitting down movement. This represents a loss of energy, so the prosthetic knee 100 may not have enough energy stored for the subsequent standing-up movement in some configurations of a prosthetic knee, without the non-linear spring feature. Even with a constant stiffness spring feature 116, though, the disclosed prosthetic knee 100 will store some energy, providing an improvement over existing devices, which have no storage in this situation. Unilateral amputees can stand up without energy storage by providing all power with their non-amputated leg. Bilateral amputees have to rely completely on their arms using prior art prosthetics and have great difficulty achieving the standing motion, if such is even possible for that user.

Figure 9:
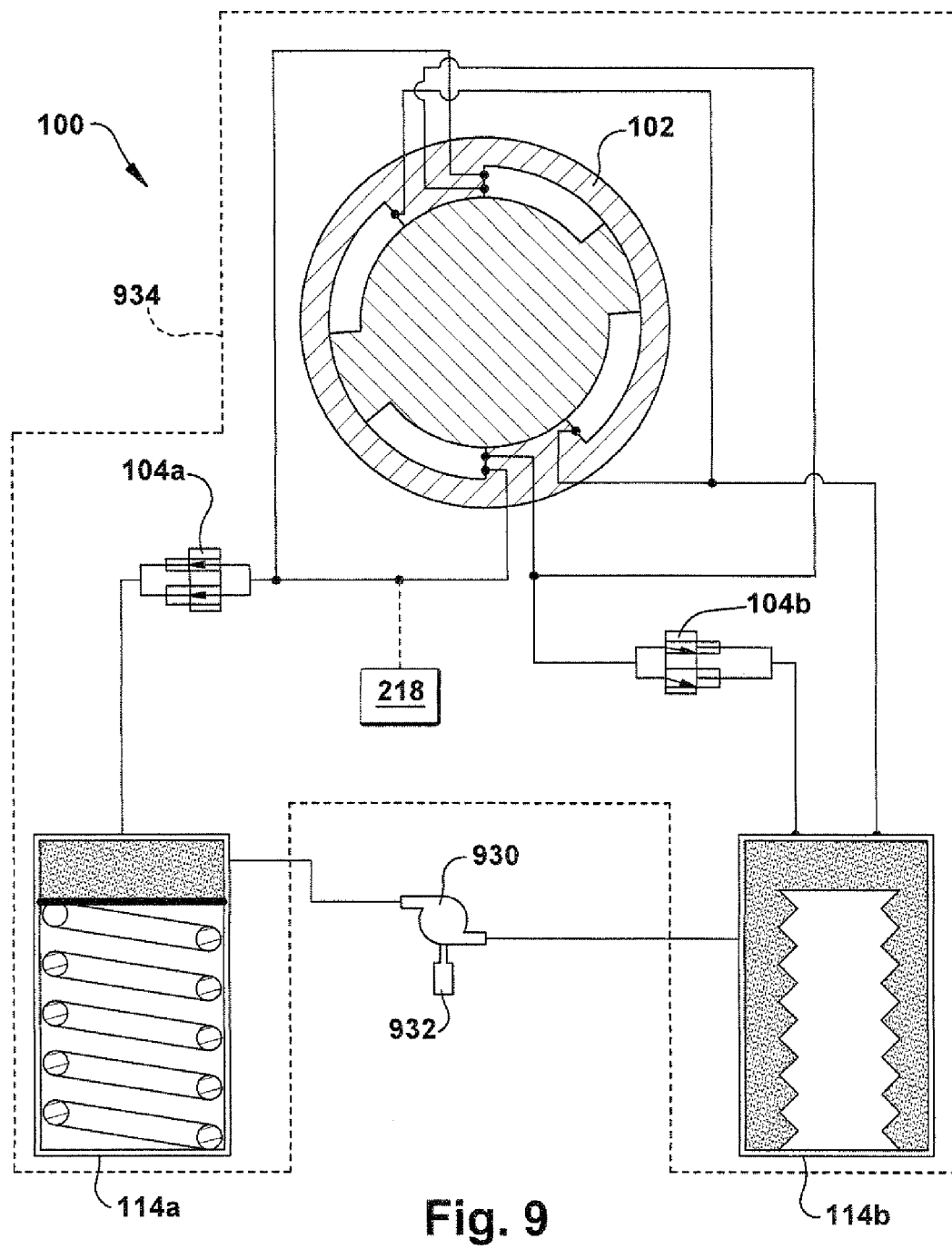
FIG. 9 is a schematic view of a hydraulic system according to a fourth arrangement of the embodiment of FIG. 1.

FIG. 9 depicts a prosthetic knee 100 similar to that of FIG. 2, but with a pump 930, driven by a motor 932 of any suitable type, located in a fluid path extending between the high- and low-pressure accumulators 114a and 114b. The motor 932 driven pump 930—shown here as an electric motor-driven fluid pump—may be helpful in providing supplemental energy to help active amputees with motions (e.g., climbing stairs) where the net positive/negative energy does not balance out across the gait cycle. As another example, when an amputee is transitioning between user tasks, the accumulator(s) 114 may not have enough stored energy for the new response mode, and supplemental energy from the pump 930 may also be helpful in providing desired force (e.g., knee torque) to bridge the transition.

As shown by the dashed line in FIG. 9, a direct drive power train 934 may comprise the accumulator(s) 114, fluid valves 104, and the control system 218. The pump 930, or any other power source, may be used to supplement charging of the accumulator(s) 114 during use. The power source (e.g., fluid pump, mechanical motor, electrical generator, or any other suitable power source) is separate from the direct drive power train 934, which allows the power source to be turned off if the "passive" energy produced by the prosthetic knee 100 system is adequate for the task at hand. If supplemental energy is needed during just a portion of the gait cycle, this "separated" power source can be run at a slower, possibly more energy-efficient speed (than that at which the direct drive power train 934 is running) throughout the gait cycle to build up an accumulator 114 charge for the portion of the gait cycle that requires a boost of supplemental energy. However, the harvested fluid energy generated by the actuator 102 and the amputee motion is still contemplated to be the primary driving energy for a prosthetic knee 100 also including a supplemental, or secondary, power source such as the pump 930.

Figure 10:
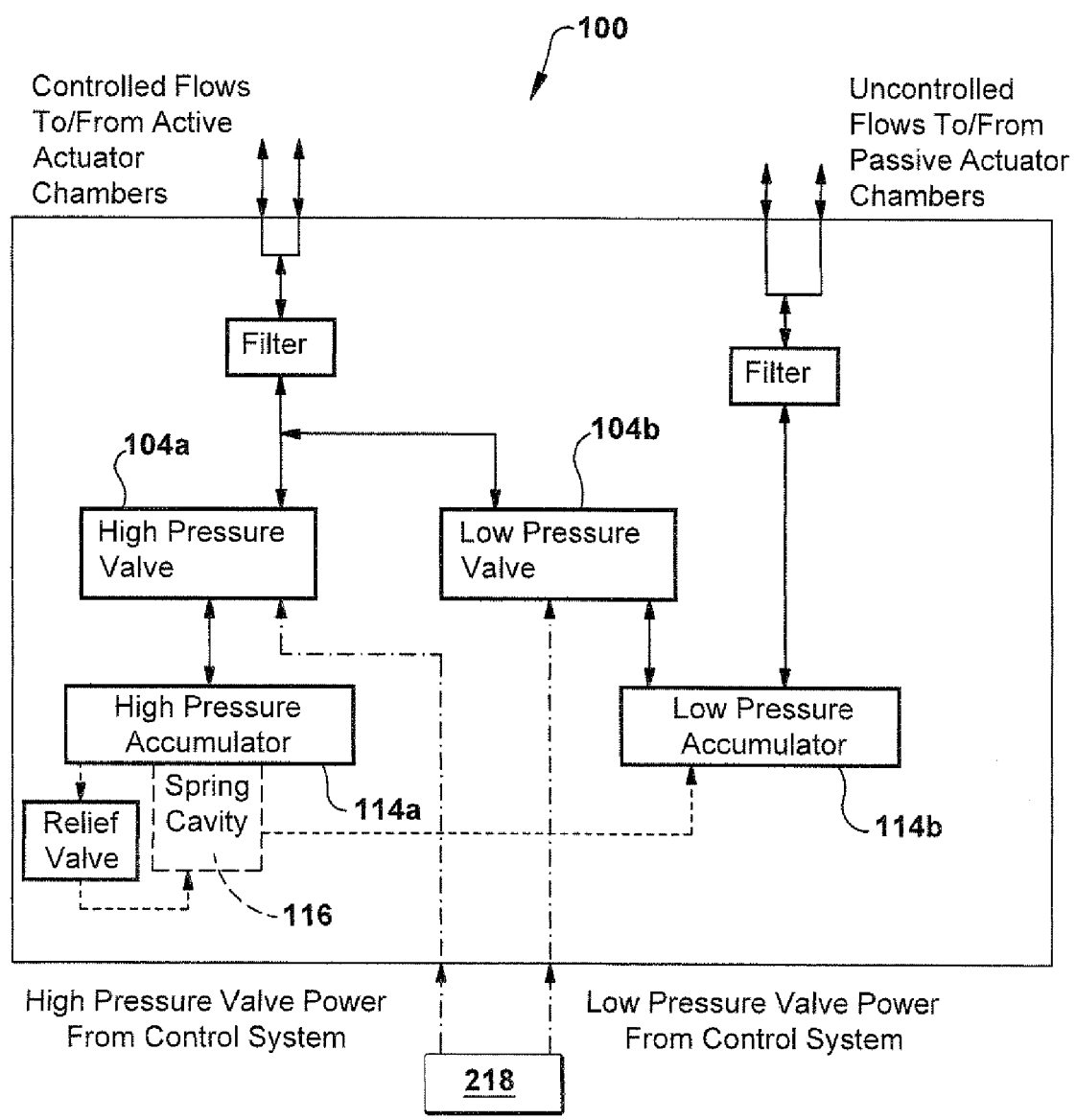
FIG. 10 schematically depicts a fluid circuit diagram according to an embodiment of the present invention.
Figure 11:
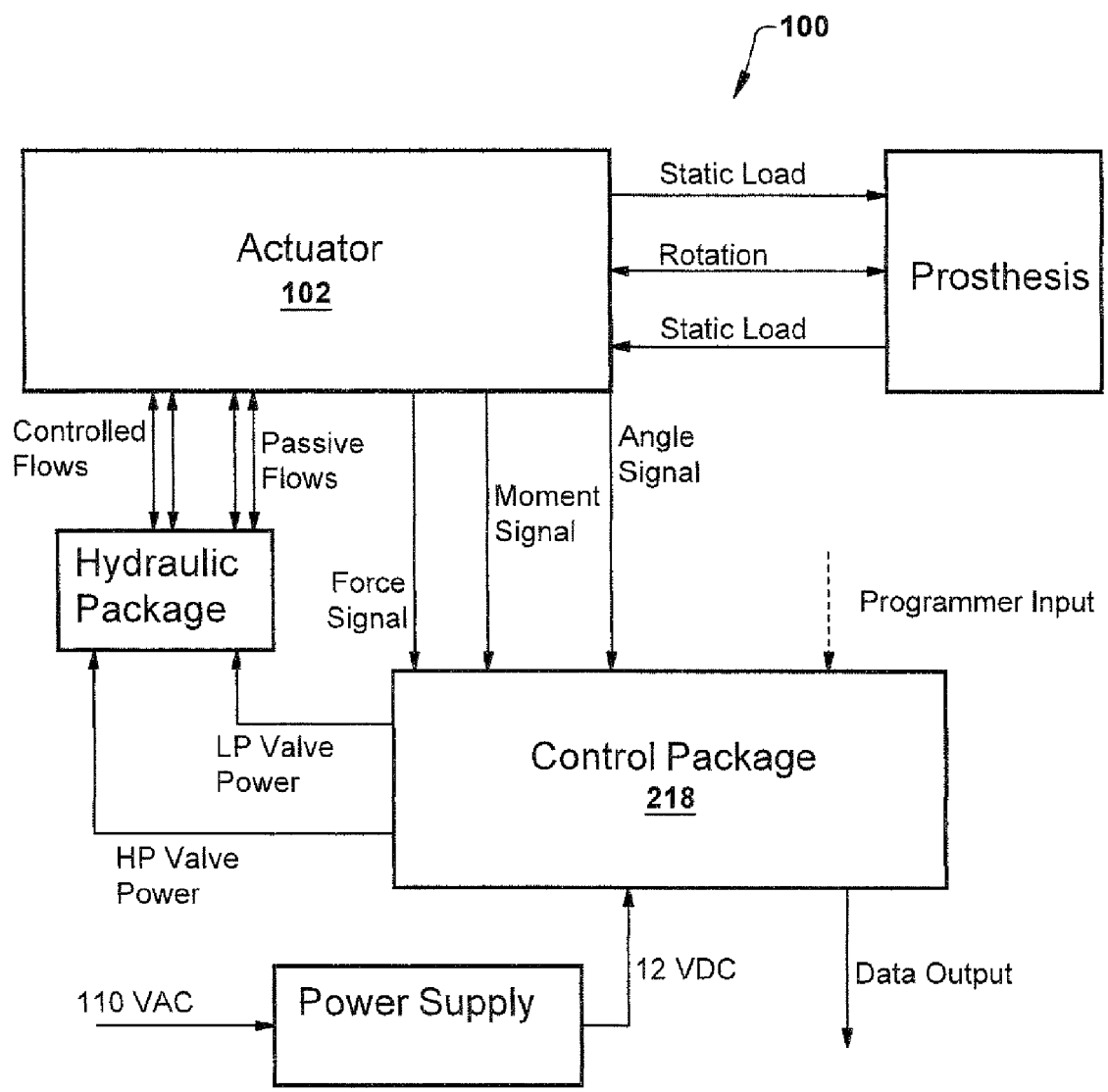
FIG. 11 schematically depicts a breadboard circuit diagram according to an embodiment of the present invention.

FIG. 10 schematically depicts a fluid circuit diagram for an example embodiment of the present invention. FIG. 11 schematically depicts a breadboard circuit diagram for an example embodiment of the present invention.

FIGS. 12A and 12B include front and rear views, respectively, of a prosthetic knee 100 in an example use environment. An upper leg structure 1236 is configured to attach to a socket (not shown) which accepts a transfemorally amputated residual limb of an amputee. A lower leg structure 1238 is hingedly connected to the upper leg structure 1236, such as via hinge 1240, and is configured to attach to a lower leg prosthesis (not shown), extending between the upper leg structure 1236 and the lower leg prosthesis. The lower an upper leg structures 1236 and 1238 are configured to move pivotally relative to one another during a gait cycle.

Figure 13:
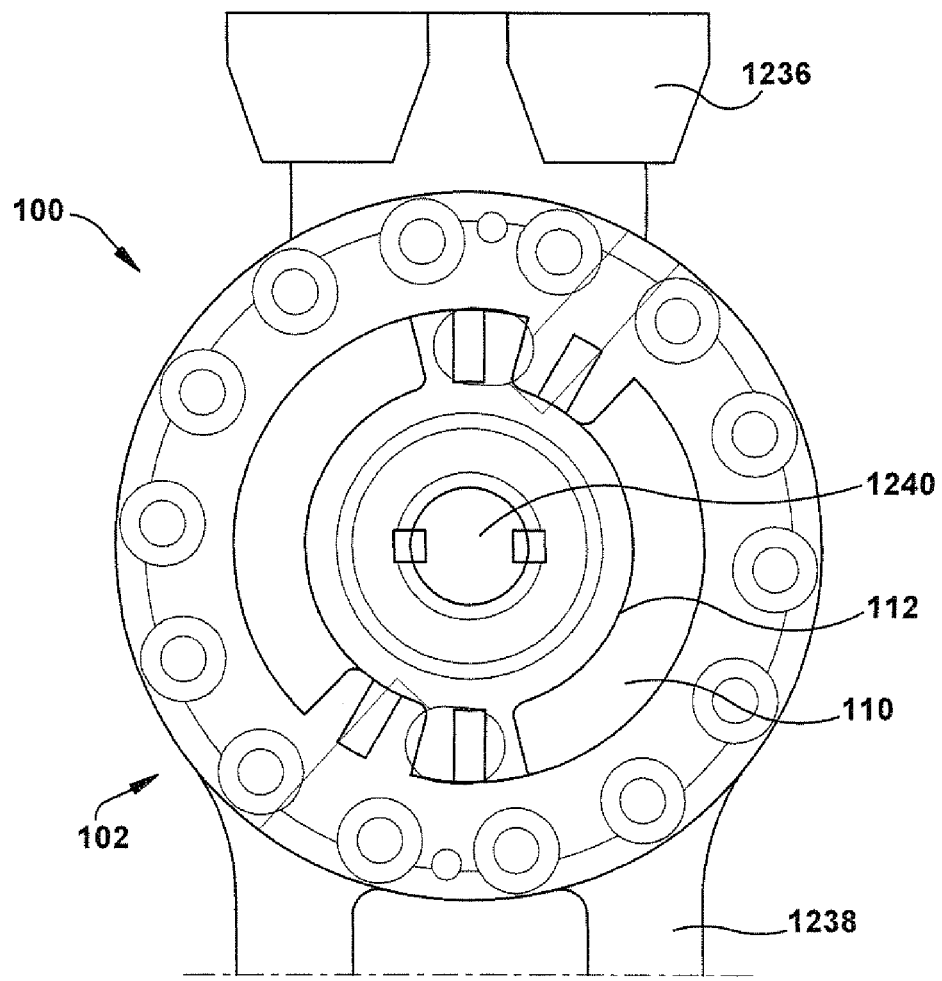
FIG. 13 is a schematic cutaway view of the embodiment of FIG. 1.

The actuator 102 (a rotary actuator is shown in FIGS. 12A-12B) is operatively connected to the upper and lower leg structures 1236 and 1238. When the amputee relatively pivots the upper and lower leg structures 1236 and 1238 (e.g., by movement of the hip and residual limb attached to the upper leg structure), the actuator 102 responsively supplies fluid energy to the accumulator(s) 114. For example, this may occur during a positive energy gait period. FIG. 13 depicts a schematic cutaway view of the rotary actuator shown in FIGS. 12A-12B.

Likewise, and generally during a negative energy gait period, the actuator 102 can brace against the upper leg structure 1236 to pivot the lower leg structure 1238 away from the upper leg structure by release of the stored fluid energy from the accumulator(s) 114 to the actuator 102.

Through use of the structures and technologies described herein, a prosthetic knee 100 can be provided which is highly customizable for a particular amputee and/or for a particular group of user tasks. When the control system 218 is tunable, energy can be harvested from, stored, and released to other portions of the amputee's body or prosthetic(s) at will and almost without restriction arising from the physical configuration of the prosthetic knee 100, in sharp contrast to prior art devices.

It is contemplated that a rheological fluid (electro-, magneto-, or other) may be used as at least a portion of the operating fluid of the prosthetic knee 100 and, if present, may be useful in providing the described response modes and/or tunability of the control system 218.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the prosthetic knee 100 are merely illustrative; one of ordinary skill in the art could readily determine any number of tools, sequences of steps, or other means/options for placing the above-described apparatus, or components thereof, into positions substantively similar to those shown and described herein. Any of the described structures and components could be integrally formed as a single unitary/monolithic piece or made up of separate sub-components, with either of these formations involving any suitable stock or bespoke components and/or any suitable material or combinations of materials. Though certain components described herein are shown as having specific geometric shapes, all structures of the present invention may have any suitable shapes, sizes, configurations, relative relationships, cross-sectional areas, or any other physical characteristics as desirable for a particular application of the present invention. The prosthetic knee 100 may include a plurality of structures cooperatively forming any components thereof and temporarily or permanently attached together in such a manner as to permit relative motion (e.g., pivoting, sliding, or any other motion) therebetween as desired. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. A Having described the invention, we claim:

1. A method of assisting a transfemoral amputee with lower limb-involving user tasks, the method comprising the steps of:
    attaching a transfemorally amputated residual limb to an upper leg structure of a prosthetic limb comprising a plurality of components including the upper leg structure, a lower leg structure, a lower leg prosthesis, a fluid actuator, a fluid, a plurality of controllable variable fluid flow resisting devices, an accumulator, and a tunable control system;
    hingedly connecting the lower leg structure to the upper leg structure;
    extending the lower leg structure between the upper leg structure and the lower leg prosthesis;
    moving the lower and upper leg structures pivotally relative to one another during a gait cycle characterized by a plurality of gait periods;
    operatively connecting the fluid actuator to the upper and lower leg structures;
    causing the fluid to flow in a predetermined manner within the fluid actuator responsive to relative pivotal movement of the upper and lower leg structures;
    providing the plurality of controllable variable fluid flow resisting devices, including first and second controllable variable fluid flow resisting devices, arranged in parallel with each other, each controllable variable fluid flow resisting device of the plurality of controllable variable fluid flow resisting devices having a different series resistance;
    providing the accumulator;
    providing the tunable control system which controls the plurality of controllable variable fluid flow resisting devices in different actuation combinations to provide a plurality of response modes, each response mode bearing a direct relationship to a desired force response of the prosthetic limb for a particular user task
    with the control system, controlling the first and second controllable variable fluid flow resisting devices to store, in the accumulator, fluid energy caused by fluid flow within the fluid actuator during gait periods of positive energy and release fluid energy to the fluid flow within the fluid actuator during gait periods of negative energy;
    controlling action of the first and second controllable variable fluid flow resisting devices with the control system in coordination with the gait of the transfemoral amputee; and
    actuating the control system to cause storage of the fluid energy for a predetermined length of time and release of the fluid energy at a predetermined time during the gait cycle, both the storage and release of the fluid energy being variable by action of the control system without replacement of components of the prosthetic limb with other, like components for the purpose of causing the variability of the storage and release of the fluid energy.

2. The method of claim 1, including the step of configuring the accumulator for variable compliance behaviour.

3. The method of claim 1, wherein the control system is a tunable control system having a plurality of predetermined response modes for operation, including the steps of:
    providing each response mode with tuned control of at least one of a starting pressure, a compliance of the accumulator, and controllable variable fluid flow resisting device resistance to flow; and
    predetermining a direct relationship of each response mode to a desired force response of the prosthetic limb for a particular user task.

4. The method of claim 3, including the step of providing the accumulator with a spring feature having at least one of a single variable-compliance spring and a nested plurality of springs to provide the plurality of predetermined response modes.

5. The method of claim 1, including the steps of:
    creating a direct drive power train comprising the accumulator and the control system; and
    providing a power source to supplement charging of the accumulator during use, the power source being separate from the direct drive power train.

6. The method of claim 1, including the step of controlling, with the control system, the first and second controllable variable fluid flow resisting devices to supplement a locomotive gait of the transfemoral amputee.

7. The method of claim 1, including the step of creating an energy receipt-storage-release cycle bearing a predetermined and supplemental relationship to a gait energy requirement cycle of a transfemoral amputee, the energy receipt-storage-release cycle being selectively variable through actuation of the control system without replacing components of the prosthetic limb with other, like components for the purpose of causing the selective variability.

8. The method of claim 1, wherein the fluid actuator is operatively connected to the upper and lower leg structures, and including the step of the transfemoral amputee relatively pivoting the upper and lower leg structures to cause the fluid actuator to supply fluid energy to the accumulator.

9. The method of claim 8, wherein the fluid actuator braces against the upper leg structure to pivot the lower leg structure away from the upper leg structure by release of the stored fluid energy from the accumulator to the fluid actuator.

10. The method of claim 1, wherein the accumulator is a high-pressure accumulator, and including the steps of:
    providing a low-pressure accumulator;
    with the control system, controlling fluid flow between the high-pressure accumulator and the fluid actuator with the first controllable variable fluid flow resisting device; and
    with the control system, controlling fluid flow between the low-pressure accumulator and the fluid actuator with the second controllable variable fluid flow resisting device.

* * * * *